United States Patent
Chessar et al.

(10) Patent No.: US 8,562,617 B2
(45) Date of Patent: Oct. 22, 2013

(54) KNEE LIGAMENT BALANCER

(75) Inventors: Ryan Chessar, Edinburgh (GB); James Drummond, Mid Calder (GB); Marc E. Ruhling, Goshen, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/478,661

(22) Filed: May 23, 2012

(65) Prior Publication Data

US 2012/0238911 A1    Sep. 20, 2012

Related U.S. Application Data

(62) Division of application No. 12/147,708, filed on Jun. 27, 2008, now Pat. No. 8,197,489.

(51) Int. Cl.
*A61B 17/58* (2006.01)
*A61B 17/88* (2006.01)

(52) U.S. Cl.
USPC ............... 606/88; 606/90; 606/102; 606/105

(58) Field of Classification Search
USPC .................... 606/86 R, 87, 88, 90, 102, 105
See application file for complete search history.

(56) References Cited

U.S. PATENT DOCUMENTS

| | | | |
|---|---|---|---|
| 4,501,266 A * | 2/1985 | McDaniel | .................. 606/90 |
| 4,795,473 A | 1/1989 | Grimes | |
| 4,796,610 A | 1/1989 | Cromartie | |
| 4,804,000 A | 2/1989 | Lamb et al. | |
| 4,808,186 A | 2/1989 | Smith | |
| 4,822,362 A | 4/1989 | Walker et al. | |
| 4,825,857 A | 5/1989 | Kenna | |
| 4,828,562 A | 5/1989 | Kenna | |
| 4,834,057 A | 5/1989 | McLeod | |
| 4,856,993 A | 8/1989 | Maness et al. | |
| 4,888,021 A | 12/1989 | Forte et al. | |
| 4,892,093 A | 1/1990 | Zarnowski et al. | |
| 4,892,546 A | 1/1990 | Kotz et al. | |
| 4,899,761 A | 2/1990 | Brown et al. | |
| 4,907,578 A | 3/1990 | Petersen | |
| 4,926,847 A | 5/1990 | Luckman | |
| 4,932,974 A | 6/1990 | Pappas et al. | |
| 4,935,023 A | 6/1990 | Whiteside et al. | |
| 4,936,853 A | 6/1990 | Fabian et al. | |
| 4,938,762 A | 7/1990 | Wehrli | |
| 4,944,756 A | 7/1990 | Kenna | |
| 4,959,071 A | 9/1990 | Brown et al. | |
| 4,963,153 A | 10/1990 | Noesberger et al. | |

(Continued)

FOREIGN PATENT DOCUMENTS

DE    10335410 A1    2/2005
EP    0720834 B1    6/1999

(Continued)

*Primary Examiner* — Michael T Schaper
(74) *Attorney, Agent, or Firm* — Barnes & Thornburg LLP

(57) ABSTRACT

An orthopaedic surgical device comprises a first sensor component and a second sensor component. Each sensor component includes a paddle set to contact a proximal tibia and a distal femur of a patient. The first sensor component and the second sensor component being movable with respect to one another to extend one paddle set beyond the other paddle set, and each paddle set includes cutouts for the clearance of the patellar tendon to avoid the need to evert the patella during use.

19 Claims, 8 Drawing Sheets

(56) References Cited

U.S. PATENT DOCUMENTS

| | | |
|---|---|---|
| 4,973,331 A | 11/1990 | Pursley et al. |
| 4,979,949 A | 12/1990 | Matsen et al. |
| 4,986,281 A | 1/1991 | Preves et al. |
| 5,002,547 A | 3/1991 | Poggie et al. |
| 5,018,514 A | 5/1991 | Grood et al. |
| 5,020,797 A | 6/1991 | Burns |
| 5,032,132 A | 7/1991 | Matsen et al. |
| 5,033,291 A | 7/1991 | Podoloff et al. |
| 5,037,423 A | 8/1991 | Kenna |
| 5,056,530 A | 10/1991 | Butler et al. |
| 5,080,675 A | 1/1992 | Lawes et al. |
| 5,082,003 A | 1/1992 | Lamb et al. |
| 5,098,436 A | 3/1992 | Ferrante et al. |
| 5,122,144 A | 6/1992 | Bert et al. |
| 5,125,408 A | 6/1992 | Basser |
| 5,129,909 A | 7/1992 | Sutherland |
| 5,197,488 A | 3/1993 | Kovacevic |
| 5,207,711 A | 5/1993 | Caspari et al. |
| 5,213,112 A | 5/1993 | Niwa et al. |
| 5,228,459 A | 7/1993 | Caspari et al. |
| 5,234,433 A | 8/1993 | Bert et al. |
| 5,234,434 A | 8/1993 | Goble |
| 5,234,435 A | 8/1993 | Seagrave |
| 5,236,432 A | 8/1993 | Matsen et al. |
| 5,250,050 A | 10/1993 | Poggie et al. |
| 5,257,996 A | 11/1993 | McGuire |
| 5,312,411 A | 5/1994 | Steele et al. |
| 5,326,363 A | 7/1994 | Aikins |
| 5,329,933 A | 7/1994 | Graf |
| 5,342,367 A | 8/1994 | Ferrante et al. |
| 5,358,527 A | 10/1994 | Forte |
| 5,360,016 A | 11/1994 | Kovacevic |
| 5,364,401 A | 11/1994 | Ferrante et al. |
| 5,364,402 A | 11/1994 | Mumme et al. |
| 5,395,401 A | 3/1995 | Bahler |
| 5,403,319 A | 4/1995 | Matsen, III et al. |
| 5,417,694 A | 5/1995 | Marik et al. |
| 5,425,775 A | 6/1995 | Kovacevic et al. |
| 5,431,652 A | 7/1995 | Shimamoto et al. |
| 5,431,653 A | 7/1995 | Callaway |
| 5,443,518 A | 8/1995 | Insall |
| 5,456,724 A | 10/1995 | Yen et al. |
| 5,470,354 A | 11/1995 | Hershberger et al. |
| 5,489,311 A | 2/1996 | Cipolletti |
| 5,496,352 A | 3/1996 | Renger |
| 5,514,144 A | 5/1996 | Bolton |
| 5,514,183 A | 5/1996 | Epstein et al. |
| 5,520,695 A | 5/1996 | Luckman |
| 5,540,696 A | 7/1996 | Booth, Jr. et al. |
| 5,562,674 A | 10/1996 | Stalcup et al. |
| 5,569,261 A | 10/1996 | Marik et al. |
| 5,571,110 A | 11/1996 | Matsen, III et al. |
| 5,571,197 A | 11/1996 | Insall |
| 5,597,379 A | 1/1997 | Haines et al. |
| 5,611,774 A | 3/1997 | Postelmans |
| 5,613,971 A | 3/1997 | Lower et al. |
| 5,630,820 A | 5/1997 | Todd |
| 5,643,272 A | 7/1997 | Haines et al. |
| 5,649,929 A | 7/1997 | Callaway |
| 5,656,785 A | 8/1997 | Trainor et al. |
| 5,658,293 A | 8/1997 | Vanlaningham |
| 5,669,914 A | 9/1997 | Eckhoff |
| 5,671,695 A | 9/1997 | Schroeder |
| 5,682,886 A | 11/1997 | Delp et al. |
| 5,683,397 A | 11/1997 | Vendrely et al. |
| 5,688,280 A | 11/1997 | Booth, Jr. et al. |
| 5,688,282 A | 11/1997 | Baron et al. |
| 5,690,635 A | 11/1997 | Matsen, III et al. |
| 5,702,422 A | 12/1997 | Stone |
| 5,702,463 A | 12/1997 | Pothier et al. |
| 5,733,292 A | 3/1998 | Gustilo et al. |
| 5,735,904 A | 4/1998 | Pappas |
| 5,743,909 A | 4/1998 | Collette |
| 5,769,894 A | 6/1998 | Ferragamo |
| 5,782,925 A | 7/1998 | Collazo et al. |
| 5,800,438 A | 9/1998 | Tuke et al. |
| 5,800,552 A | 9/1998 | Forte |
| 5,810,827 A | 9/1998 | Haines et al. |
| 5,824,104 A | 10/1998 | Tuke |
| 5,840,047 A | 11/1998 | Stedham |
| 5,860,980 A | 1/1999 | Axelson et al. |
| 5,871,018 A | 2/1999 | Delp et al. |
| 5,879,389 A | 3/1999 | Koshino |
| 5,880,976 A | 3/1999 | DiGioia III et al. |
| 5,891,150 A | 4/1999 | Chan |
| 5,911,723 A * | 6/1999 | Ashby et al. .................. 606/88 |
| 5,935,086 A | 8/1999 | Beacon et al. |
| 6,019,767 A | 2/2000 | Howell |
| 6,022,377 A | 2/2000 | Nuelle et al. |
| 6,034,296 A | 3/2000 | Elvin et al. |
| 6,056,752 A | 5/2000 | Roger |
| 6,056,754 A | 5/2000 | Haines et al. |
| 6,056,756 A | 5/2000 | Eng et al. |
| 6,080,154 A | 6/2000 | Reay-Young et al. |
| 6,086,592 A | 7/2000 | Rosenberg et al. |
| 6,096,043 A | 8/2000 | Techiera et al. |
| 6,102,952 A | 8/2000 | Koshino |
| 6,113,604 A | 9/2000 | Whittaker et al. |
| 6,126,692 A | 10/2000 | Robie et al. |
| 6,174,294 B1 | 1/2001 | Crabb et al. |
| 6,447,448 B1 | 9/2002 | Ishikawa et al. |
| 6,488,711 B1 | 12/2002 | Grafinger |
| 6,553,681 B2 | 4/2003 | Ekholm, Jr. et al. |
| 6,575,980 B1 | 6/2003 | Robie et al. |
| 6,589,283 B1 | 7/2003 | Metzger et al. |
| 6,610,096 B2 | 8/2003 | MacDonald |
| 6,632,225 B2 | 10/2003 | Sanford et al. |
| 6,648,896 B2 | 11/2003 | Overes et al. |
| 6,702,821 B2 | 3/2004 | Bonutti |
| 6,706,005 B2 | 3/2004 | Roy et al. |
| 6,758,850 B2 | 7/2004 | Smith et al. |
| 6,770,078 B2 | 8/2004 | Bonutti |
| 6,821,299 B2 | 11/2004 | Kirking et al. |
| 6,827,723 B2 | 12/2004 | Carson |
| 6,905,513 B1 | 6/2005 | Metzger |
| 6,923,817 B2 | 8/2005 | Carson et al. |
| 6,972,039 B2 | 12/2005 | Metzger et al. |
| 6,984,249 B2 | 1/2006 | Keller |
| 7,104,996 B2 | 9/2006 | Bonutti |
| 7,153,281 B2 | 12/2006 | Holmes |
| 7,412,897 B2 | 8/2008 | Crottet et al. |
| 7,559,931 B2 | 7/2009 | Stone |
| 8,137,361 B2 * | 3/2012 | Duggineni et al. ............ 606/102 |
| 8,231,631 B2 * | 7/2012 | Lavallee et al. .................. 606/90 |
| 8,323,290 B2 * | 12/2012 | Metzger et al. .................. 606/90 |
| 2002/0029045 A1 | 3/2002 | Bonutti |
| 2002/0052606 A1 | 5/2002 | Bonutti |
| 2002/0133175 A1 | 9/2002 | Carson |
| 2002/0147455 A1 | 10/2002 | Carson |
| 2002/0156480 A1 * | 10/2002 | Overes et al. .................. 606/90 |
| 2003/0028196 A1 | 2/2003 | Bonutti |
| 2003/0069591 A1 | 4/2003 | Carson et al. |
| 2003/0069644 A1 | 4/2003 | Kovacevic et al. |
| 2003/0130665 A1 | 7/2003 | Pinczewski |
| 2003/0144669 A1 | 7/2003 | Robinson |
| 2003/0153978 A1 | 8/2003 | Whiteside |
| 2003/0187452 A1 | 10/2003 | Smith et al. |
| 2003/0236472 A1 | 12/2003 | Van Hoeck et al. |
| 2004/0019382 A1 | 1/2004 | Amirouche et al. |
| 2004/0064073 A1 | 4/2004 | Heldreth |
| 2004/0064191 A1 | 4/2004 | Wasielewski |
| 2004/0097951 A1 | 5/2004 | Steffensmeier |
| 2004/0243148 A1 | 12/2004 | Wasielewski |
| 2005/0021044 A1 | 1/2005 | Stone et al. |
| 2005/0038442 A1 * | 2/2005 | Freeman .................. 606/86 |
| 2005/0113846 A1 | 5/2005 | Carson |
| 2005/0149041 A1 | 7/2005 | McGinley et al. |
| 2005/0177169 A1 | 8/2005 | Fisher et al. |
| 2005/0177170 A1 | 8/2005 | Fisher et al. |
| 2005/0234332 A1 | 10/2005 | Murphy |
| 2005/0234448 A1 | 10/2005 | McCarthy |
| 2005/0234465 A1 | 10/2005 | McCombs |
| 2005/0234466 A1 | 10/2005 | Stallings |
| 2005/0234468 A1 | 10/2005 | Carson |

(56) References Cited

U.S. PATENT DOCUMENTS

| | | |
|---|---|---|
| 2005/0251026 A1 | 11/2005 | Stone |
| 2005/0267485 A1 | 12/2005 | Cordes et al. |
| 2006/0081063 A1* | 4/2006 | Neubauer et al. ............... 73/818 |
| 2006/0149277 A1 | 7/2006 | Cinquin et al. |
| 2006/0161051 A1 | 7/2006 | Terrill-Grisoni et al. |
| 2006/0224088 A1 | 10/2006 | Roche |
| 2006/0241569 A1* | 10/2006 | DiSilvestro ..................... 606/1 |
| 2006/0271056 A1 | 11/2006 | Terrill-Grisoni et al. |
| 2007/0162142 A1 | 7/2007 | Stone |
| 2007/0233144 A1* | 10/2007 | Lavallee et al. ................ 606/90 |
| 2007/0239165 A1 | 10/2007 | Amirouche |
| 2007/0244488 A1 | 10/2007 | Metzger et al. |
| 2008/0058946 A1* | 3/2008 | Dietz ......................... 623/20.32 |
| 2008/0306413 A1 | 12/2008 | Crottet et al. |
| 2009/0005708 A1 | 1/2009 | Johanson et al. |
| 2009/0018544 A1* | 1/2009 | Heavener ....................... 606/90 |
| 2009/0099570 A1 | 4/2009 | Paradis et al. |
| 2009/0138019 A1 | 5/2009 | Wasielewski |
| 2009/0138021 A1 | 5/2009 | Colquhoun |
| 2009/0270869 A1 | 10/2009 | Colquhoun et al. |
| 2009/0318836 A1 | 12/2009 | Stone et al. |
| 2009/0318930 A1 | 12/2009 | Stone et al. |
| 2009/0318931 A1 | 12/2009 | Stone et al. |
| 2009/0326544 A1 | 12/2009 | Chessar et al. |
| 2010/0016705 A1 | 1/2010 | Stone |
| 2010/0023067 A1* | 1/2010 | DiSilvestro ................ 606/86 R |
| 2010/0063508 A1 | 3/2010 | Borja et al. |
| 2010/0063509 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0137869 A1 | 6/2010 | Borja et al. |
| 2010/0137871 A1 | 6/2010 | Borja |
| 2010/0249660 A1* | 9/2010 | Sherman et al. .............. 600/587 |
| 2010/0249777 A1* | 9/2010 | Sherman et al. ................ 606/53 |
| 2010/0249789 A1* | 9/2010 | Rock et al. ...................... 606/88 |
| 2012/0071881 A1* | 3/2012 | Lang et al. ...................... 606/87 |
| 2012/0172762 A1* | 7/2012 | Boyer et al. .................. 600/587 |
| 2012/0232429 A1* | 9/2012 | Fischer et al. ................ 600/592 |
| 2013/0023794 A1* | 1/2013 | Stein et al. .................... 600/587 |

FOREIGN PATENT DOCUMENTS

| | | |
|---|---|---|
| EP | 1348382 A2 | 10/2003 |
| EP | 1707159 B1 | 11/2008 |
| EP | 1402857 B1 | 8/2010 |
| EP | 1915951 B1 | 6/2011 |
| WO | 9617552 A1 | 6/1996 |
| WO | 9935972 | 7/1999 |
| WO | 03065949 A2 | 8/2003 |
| WO | 2004008988 A2 | 1/2004 |
| WO | 2005023120 A1 | 3/2005 |
| WO | 2005089681 A | 9/2005 |
| WO | 2007036694 A1 | 4/2007 |
| WO | 2007036699 A1 | 4/2007 |
| WO | 2010011978 A1 | 1/2010 |
| WO | 2010022272 A1 | 2/2010 |
| WO | 2010030809 A1 | 3/2010 |

* cited by examiner

KNEE LIGAMENT BALANCER

This application is a divisional of U.S. patent application Ser. No. 12/147,708, filed on Jun. 27, 2008 and issued as U.S. Pat. No. 8,197,489 on Jun. 12, 2012. That application is incorporated in its entirety herein by reference.

CROSS-REFERENCE TO RELATED U.S. PATENT APPLICATION

Cross-reference is made to U.S. Utility patent application Ser. No. 11/094,956 entitled "Method and Apparatus for use in Balancing Ligaments of a Knee" by Mark R. DiSilvestro, which was filed on Mar. 31, 2005, the entirety of which is incorporated herein by reference.

TECHNICAL FIELD

The present disclosure relates generally to devices and methods for use in the performance of orthopaedic surgical procedures such as knee replacement procedures.

BACKGROUND

In some orthopaedic surgical procedures, such as a total knee replacement procedure, ligament balancing devices (commonly known as ligament balancers) may be used to balance the surrounding soft tissue (i.e., ligaments) of a patient's joint. For example, in a total knee replacement procedure, ligament balancing may be performed to ensure a generally rectangular shaped extension gap and a generally rectangular shaped flexion gap at a predetermined joint force value between the patient's natural or prosthetic proximal tibia and the patient's natural or prosthetic distal femur.

To do so, a ligament balancer may be used to measure the medial and lateral joint forces and the medial and lateral gap displacements when the patient's leg is in extension (i.e., the patient's tibia is positioned at about 0 degrees relative to the patient's femur) and in flexion (i.e., the patient's tibia is positioned at about 90 degrees relative to the patient's femur). In either extension or flexion, if the medial and lateral gap displacements are not approximately equal (i.e., do not form a generally rectangular shaped joint gap) at the predetermined joint force value, ligament release may be performed to equalize the medial and/or lateral gap displacements.

SUMMARY

An orthopaedic surgical device may include a first sensor component and a second sensor component. The first sensor component may include a first paddle set and the second sensor component may include a second paddle set. The first sensor component and the second sensor component may be movable with respect to one another to extend one paddle set beyond the other paddle set.

Moreover, the posterior ends of the extended paddle set and the other paddle set may be inserted into a side of a patient's knee without everting a patella of the knee. The posterior ends of the extended paddle set may contact portions of a tibia and femur that lie away from the side into which the posterior ends of the extended paddle set were inserted. The posterior ends of the other paddle set may contact portions of the tibia and the femur that lie toward the side into which the posterior ends of the paddle set were inserted.

BRIEF DESCRIPTION OF THE DRAWINGS

The invention described herein is illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements.

DETAILED DESCRIPTION OF THE DRAWINGS

Figure 1:
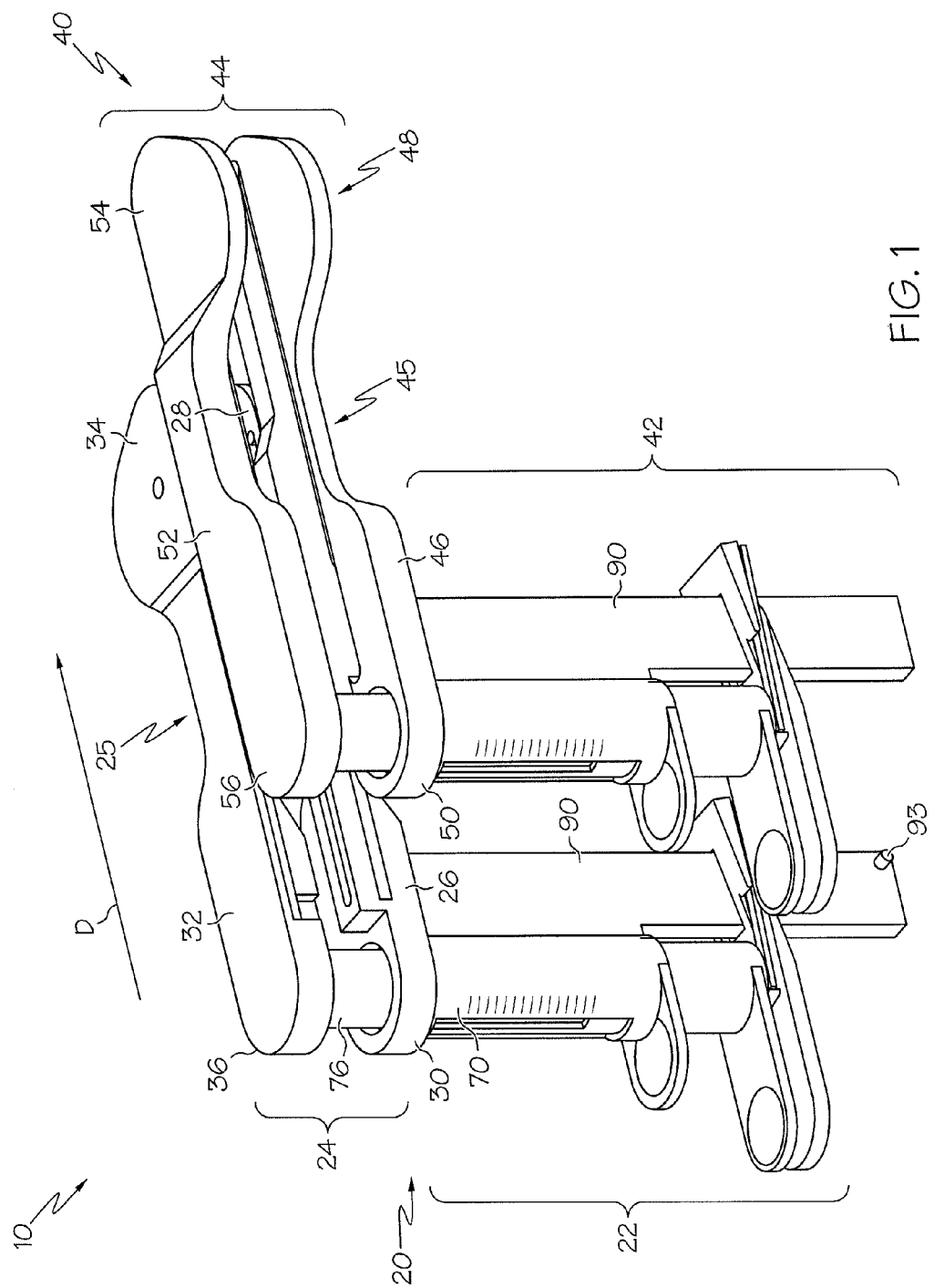
FIGS. 1-4 show various perspective views of an embodiment of a ligament balancer.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Moreover, the following description and claims use the terms "first" and "second" to succinctly and distinctly identify similar components. However, it should be appreciated that the terms "first" and "second" in the following description and claims are used merely for convenience of description and are not meant to require a sequential or ordered relationship between such components.

Figure 2:
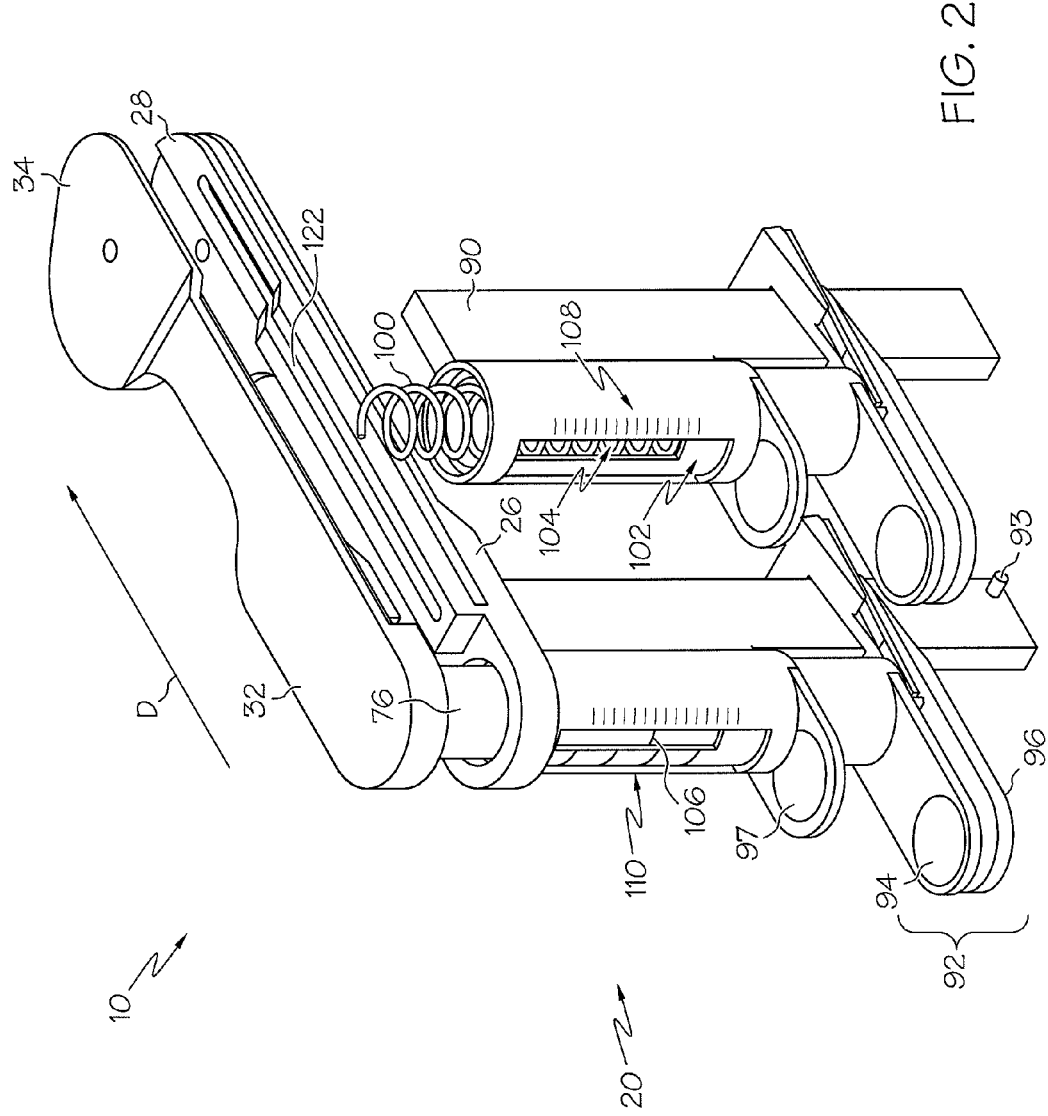
Figure 3:
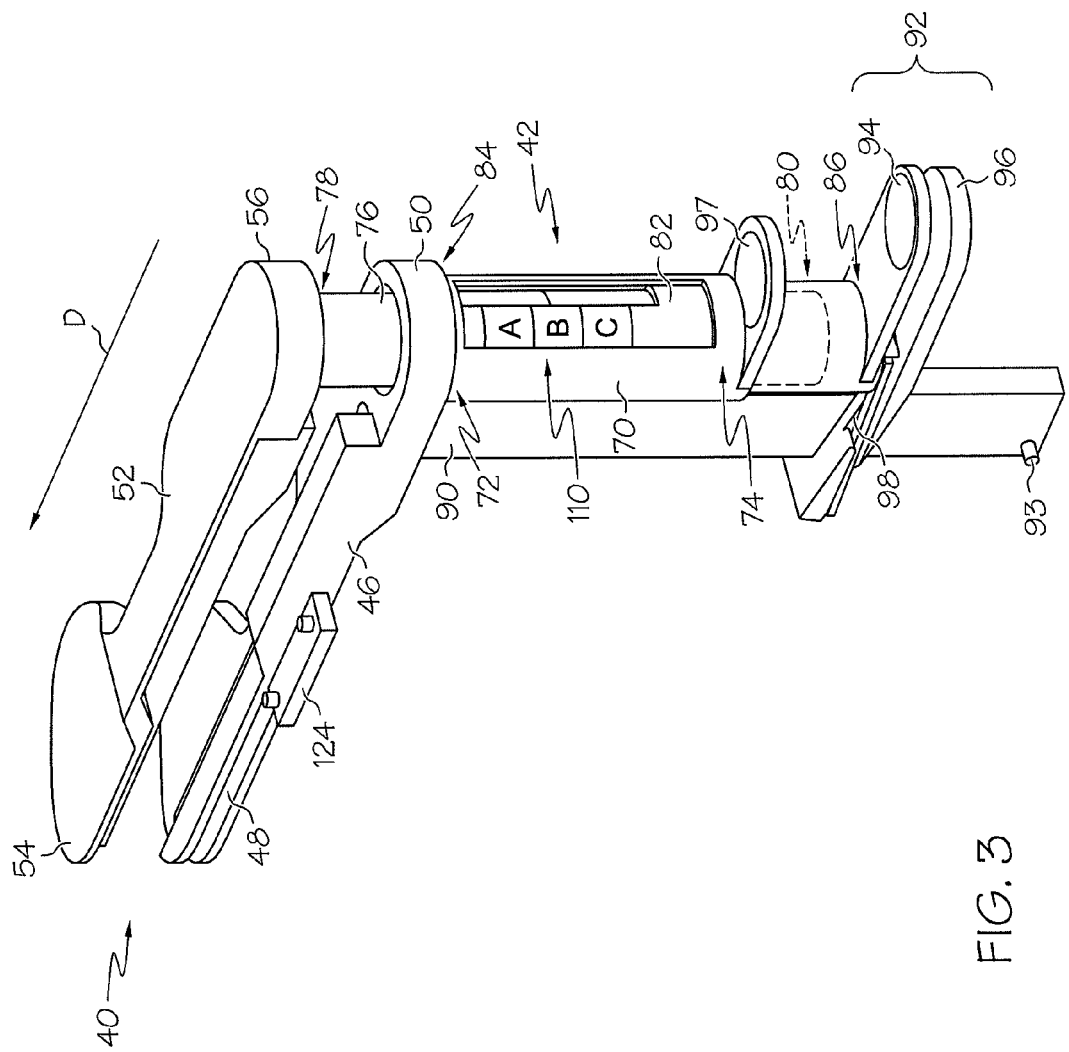
Figure 4:
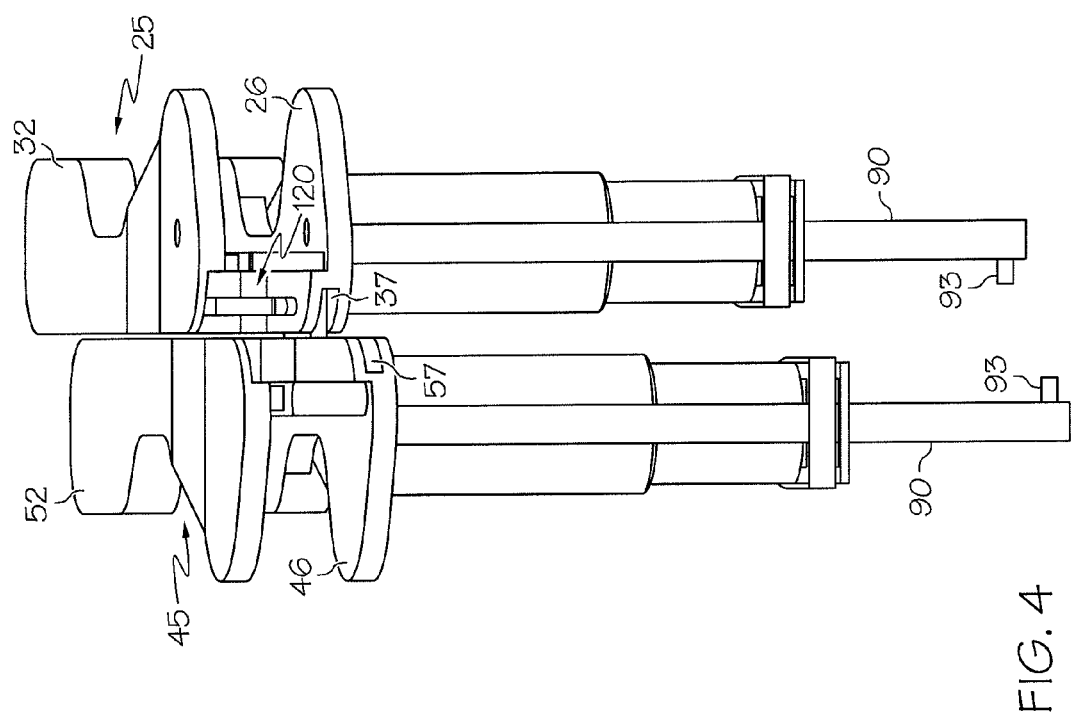

Referring to FIGS. 1-5, an embodiment of a ligament balancer 10 for use in an orthopaedic surgical procedure is shown. The ligament balancer 10 may include a sensor component 20 which is slideably coupled to a sensor component 40 via a sliding mechanism 120 (FIG. 4). As shown in FIG. 1, the sensor component 20 may include a support 22 from which a paddle set 24 extends in a general extension direction D. The paddle set 24 may include a tibial paddle 26 having a posterior end 28 to contact a proximal tibia 210 (FIG. 8) and an anterior end 30 coupled to the support 22. The paddle set 24 may further include a femoral paddle 32 having a posterior end 34 to contact a distal femur 220 (FIG. 8) and an anterior end 36 coupled to the support 22. Furthermore, as shown in FIG. 4, the tibial paddle 26 may include a mounting slot or aperture 37 configured to receive additional instrumentation such as a flexion adapter, a distal femoral cutting block, and/or an anterior/posterior resection guide.

Similarly, the sensor component 40 may include a support 42 from which a paddle set 44 extends in a general extension direction D. The paddle set 44 may include a tibial paddle 46 having a posterior end 48 to contact a proximal tibia 210 (FIG. 8) and an anterior end 50 coupled to the support 42. The paddle set 44 may further include a femoral paddle 52 having a posterior end 54 to contact a distal femur 220 (FIG. 8) and an anterior end 56 coupled to the support 42. Furthermore, as shown in FIG. 4, the tibial paddle 46 may include a mounting slot or aperture 57 configured to receive additional instrumentation such as a flexion adapter, a distal femoral cutting block, and/or an anterior/posterior resection guide.

As explained in more detail below, the support 22 generally defines a sensor to sense a displacement between paddles 26, 32 of the paddle set 24 and a tensor to sense and/or provide a force between paddles 26, 32 of the paddle set 24. Similarly, the support 42 generally defines a sensor to sense a displacement between paddles 46, 52 of the paddle set 44 and a tensor to sense and/or provide a force between paddles 46, 52 of the paddle set 44.

Figure 8:
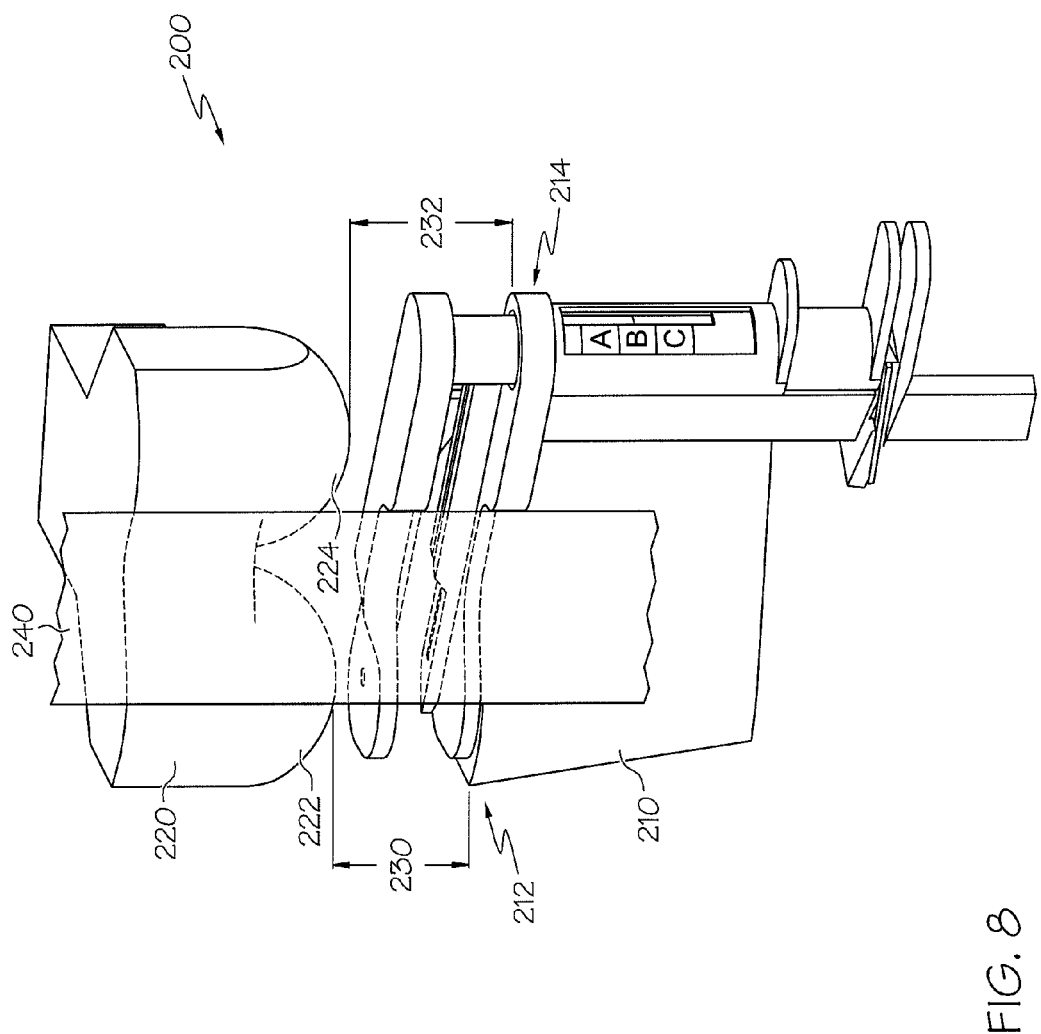
FIG. 8 shows a first sensor component interfacing with a distal femur and a proximal tibia.

Moreover, the support 22 permits movement of the femoral paddle 32 with respect to the tibial paddle 26 to determine a displacement 230 between a portion 212 of the proximal tibia 210 and a condyle 222 of the distal femur 220. See, FIG. 8. Likewise, the support 42 permits movement of the femoral paddle 52 with respect to the tibial paddle 46 to determine a displacement 232 between a portion 214 of the proximal tibia 210 and a condyle 224 of the distal femur 220. Referring to FIGS. 1 and 8, the paddle set 24 and paddle set 44 may have patellar tendon cutouts 25, 45 to permit entry of the paddle set 24 and the paddle set 44 into the knee without everting the patella and the patellar tendon 240 as the cutouts 25, 45 provide clearance between the paddle sets 24, 44 and the patellar tendon 240.

Referring now to FIGS. 1 and 3, each support 22, 42 includes a housing 70 having an upper end 72 and a lower end 74, a displacement cylinder 76 having an upper end 78 and a lower end 80, and a tensor cylinder 82 having an upper end 84 and a lower end 86. As shown, an anterior end 30, 50 of each tibial paddle 26, 46 may be coupled to a respective housing 70 such that each tibial paddle 26, 46 generally extends away from the housings 70 in the extension direction D. Further, an anterior end 36, 56 of each femoral paddle 32, 52 may be coupled to a respective displacement cylinder 76 such that each femoral paddle 32, 52 generally extends away from the displacement cylinder 76 in the extension direction D.

The housing 70, displacement cylinder 76 and tensor cylinder 82 of each support 22, 42 may be telescopically coupled to one another. To this end, the housing 70 and each cylinder 76, 82 in one embodiment comprises a circular cross section and a slightly different internal and external diameter. However, it should be appreciated that the housing 70 and cylinders 76, 82 may comprise other shapes such as, for example, square, oval, triangular or other cross sections. Each tensor cylinder 82 may be telescopically coupled with a corresponding housing 70. In particular, in one embodiment, the upper end 84 of the tensor cylinder 82 may be inserted into the lower end 74 of the housing 70 permitting movement of the lower end 86 of the tensor cylinder 82 in relation to the lower end 74 of the housing 70 as the tensor cylinder 82 is extended from or retracted into the housing 70.

Each displacement cylinder 76 may be telescopically coupled with a corresponding tensor cylinder 82 and housing 70. In particular, in one embodiment, the lower end 80 of a displacement cylinder 76 may be inserted into the upper end 84 of a tensor cylinder 82 permitting movement of the upper end 78 of the displacement cylinder 76 in relation to the lower end 86 of the tensor cylinder 82 as the displacement cylinder 76 extends from or retracts into the tensor cylinder 82. As should be appreciated, telescopically coupling the displacement cylinder 76 with the tensor cylinder 82 also telescopically couples the displacement cylinder 76 with the housing 70 due to the displacement cylinder 76 being telescopically coupled with the tensor cylinder 82.

Each support 22, 42 further includes a rail 90 coupled to the housing 70 such that a distal end of the rail 90 extends beyond the lower end 74 of the housing 70. A locking mechanism 92 couples the tensor cylinder 82 to the rail 90. In particular, the locking mechanism 92, when locked, prevents the tensor cylinder 82 from moving in relation to the housing 70. When released or unlocked, the locking mechanism 92 slides along the rail 90 thus permitting the tensor cylinder 82 to be moved in relation to the housing 70. More specifically, when unlocked, the tensor cylinder 82 may be extended from the housing 70 thus resulting in the lower end 86 of the tensor cylinder 82 being extended away from the lower end 74 of the housing 70, or the tensor cylinder 82 may be retracted into the housing 70 thus resulting in the lower end 86 of the tensor cylinder 82 being retracted toward the lower end 74 of the housing 70. Furthermore, a pin or stop 93 on the rail 90 may prevent over extending the tensor cylinder 82 and/or accidentally sliding the locking mechanism 92 off the rail 90.

In the embodiment shown in FIGS. 1-4, the tensor cylinder 82 includes a lever 94 coupled toward the lower end 86 to aid in extending or retracting the tensor cylinder 82. Moreover, the locking mechanism 92 includes a release lever 96 aligned with the lever 94 of the tensor cylinder 82. In operation, the user may squeeze the lever 94 and release lever 96 together in order to unlock the tensor cylinder 82 and adjust the position of the tensor cylinder 82. A leaf spring 98 of the locking mechanism 92 may return the locking mechanism 92 to a locked state in response to the user releasing the lever 94 and release lever 96, thus locking the tensor cylinder 82 into place.

Furthermore, the housing 70 includes a lever 97 coupled toward the lower end 74 to aid in adjusting displacement between paddles of the corresponding paddle set 24, 44. It should be appreciated that raising the lever 97 with respect to a locked lever 94 generally results in reducing the displacement between paddles of the corresponding paddle set 24, 44. Conversely, lowering the lever 97 with respect to the locked lever 94 generally results in increasing the displacement between paddles of the corresponding paddle set 24, 44.

Figure 5:
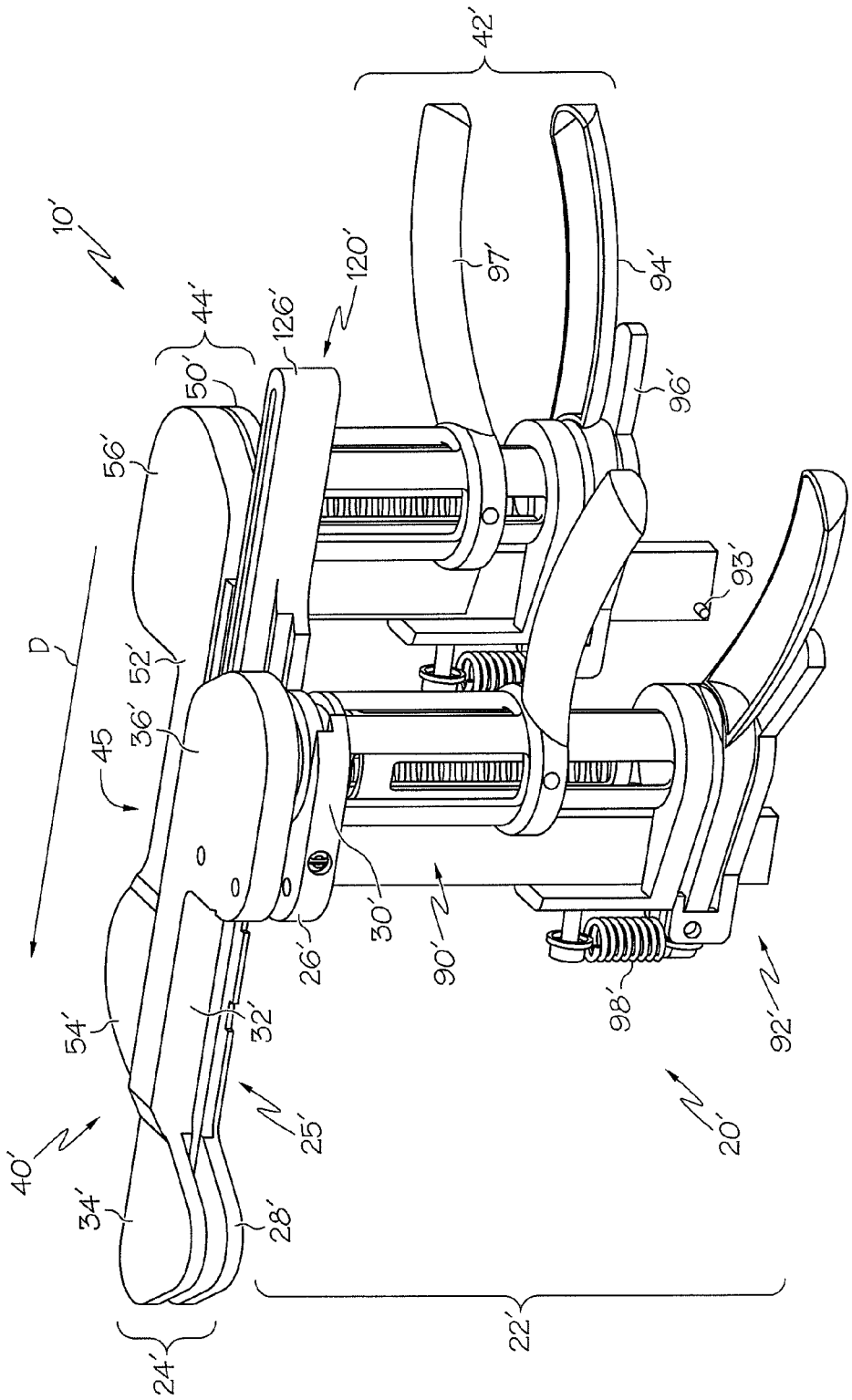
FIGS. 5-6 show perspective views of another embodiment of a ligament balancer.
Figure 6:
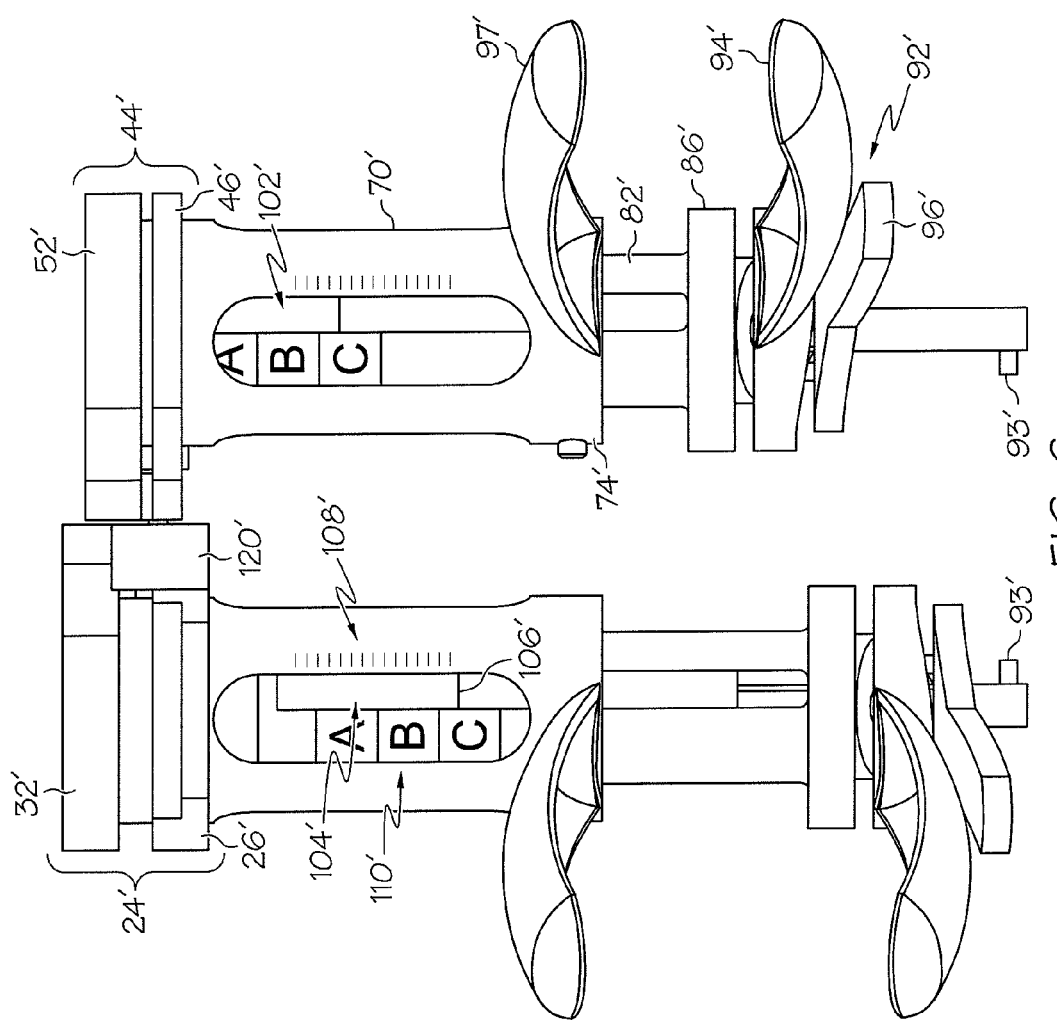

In another embodiment of a ligament balancer 10' shown in FIGS. 5-6, the tensor cylinder 82' includes a handle 94' coupled toward the lower end 86' of the tensor cylinder 82' to aid in extending or retracting the tensor cylinder 82'. Moreover, the locking mechanism 92' includes a release lever 96' aligned with the handle 94' but shorter in length than the handle 94' to permit use of the handle 94' without releasing the locking mechanism 92'. The locking mechanism 92' further includes an extension spring 98' coupled to the rail 90' and the release lever 96' to return the locking mechanism 92' to a locked state in response to the user releasing the release lever 96'.

Furthermore, the housing 70' includes a lever 97' coupled toward the lower end 74' to aid in adjusting displacement between paddles of the corresponding paddle set 24', 44'. It should be appreciated that raising the lever 97' with respect to a locked lever 94' generally results in reducing the displacement between paddles of the corresponding paddle set 24', 44'. Conversely, lowering the lever 97' with respect to the locked lever 94' generally results in increasing the displacement between paddles of the corresponding paddle set 24', 44'.

As shown in FIG. 2, each support 22, 42 may include a compression spring 100 positioned within and coaxial to the housing 70, displacement cylinder 76, and tensor cylinder 82.

In particular, the spring 100 may be positioned between the lower end 86 of the tensor cylinder 82 and the upper end 78 of the displacement cylinder 76. The spring 100 may assert a force between the lower end 86 of the tensor cylinder 82 and the upper end 78 of displacement cylinder 76. A user of the ligament balancer 10 may selectably adjust the load upon the compression spring 100 by releasing the locking mechanism 92 and extending or retracting the tensor cylinder 82 via levers 94, 96. The load upon the compression spring 100 results in the compression spring 100 applying a force to the displacement cylinder 76 which translates the selectable force to the femoral paddle 32, 52 of the corresponding paddle set 24, 44.

The housing 70 and tensor cylinder 82 respectively include openings 102, 104. The housing opening 102 and tensor opening 104 are aligned such that an indicator 106 upon the displacement cylinder 76 may be viewed through the openings 102, 104. Since the tibial paddles 26, 46, in one embodiment, are stationary with respect to the corresponding housings 70, movement of the indicator 106 in relation to the housing 70 corresponds to movement of the corresponding femoral paddle 32, 52 to its corresponding tibial paddle 26, 46. Accordingly, the housing 70, in one embodiment, includes a displacement scale 108 which relates the position of the indicator 106 relative to the housing 70 to the displacement of the corresponding femoral paddle 32, 52 from its corresponding tibial paddle 26, 46.

Since compression spring 100 is positioned between the lower end 86 of the tensor cylinder 82 and the upper end 78 of the displacement cylinder 76 in one embodiment, movement of the indicator 106 in relation to the tensor cylinder 82 corresponds to the load upon the compression spring 100 and the selectable force applied between paddles of the corresponding paddle set 24, 44. Accordingly, the tensor cylinder 82, in one embodiment, includes force ranges 110 which relate the position of the indicator 106 relative to the tensor cylinder 82 to the force applied between the corresponding paddle set 24, 44. In one embodiment, the tensor cylinder 82 includes three force ranges labeled A, B and C in the figures. However, other embodiments may include a different number of force ranges or may include a force scale providing a measurement of the force applied to the corresponding paddle set 24, 44 instead of or in addition to an indication of a general range.

As mentioned above, the sensor component 20 is slideably coupled to the sensor component 40 via a sliding mechanism 120 (FIG. 4). The sliding mechanism 120 generally permits extending the posterior ends of one paddle set 24, 44 in the extension direction D so that posterior ends of the extended paddle set 24, 44 extend beyond in posterior ends of the other paddle set 24, 44. As shown in FIGS. 2 and 3, the sliding mechanism 120 in one embodiment may include a track 122 and a runner 124. The track 122 may be coupled to or otherwise incorporated into the tibial paddle 26. The track 122 may also run generally along the length of the tibial paddle 26 in the extension direction D between its anterior end 30 and the posterior end 28. The runner 124 may be coupled to or otherwise incorporated into the tibial paddle 46 near a midpoint between its posterior end 48 and anterior end 50. In another embodiment, the track 122 is coupled to the tibial paddle 46 and the runner 124 is coupled to the tibial paddle 26.

The runner 124 may be slideably coupled to the track 122 thereby slideably coupling the sensor component 40 to the sensor component 20. In particular, the runner 124 may be restricted to movement along the track 122 in the extension direction D. Accordingly, moving the sensor component 20 in the extension direction D with respect to the sensor component 40 results in the runner 124 of the sliding mechanism 120 following the track 122 in the extension direction D.

Referring now to FIGS. 5-6 another embodiment of the sliding mechanism is shown. The sliding mechanism 120' of FIGS. 5-6 may include a track and a runner similar to the track 122 (FIG. 2) and runner 124 (FIG. 3) of the balancer 10. The track may be coupled to or otherwise incorporated into the tibial paddle 26'. The track may also extend beyond an anterior end 30' of the tibial paddle 26' and may run generally between its extended anterior end 126' and a point between the posterior end 28' and the anterior end 30' of the tibial paddle 26'. The runner may be coupled to or otherwise incorporated into the tibial paddle 46' near a point near its anterior end 50'. In another embodiment, the track is coupled to the tibial paddle 46' and the runner is coupled to the tibial paddle 26'.

The runner may be slideably coupled to the track thereby slideably coupling the sensor component 40' to the sensor component 20'. In particular, the runner may be restricted to movement along the track in the extension direction D. Accordingly, moving the sensor component 20' in the extension direction D with respect to the sensor component 40' results in the runner of the sliding mechanism 120' following the track in the extension direction D.

In the above ligament balancers 10, 10', movement of the femoral paddles may generally be performed manually as a result of actuating the locking mechanisms 92, 92' and levers and/or handles of the ligament balancers 10, 10'. The ligament balancer 10" shown in FIG. 7, however, replaces the manual controls of the ligament balancers 10, 10' with automated mechanisms. In particular, the ligament balancer 10" may include a force sensor 330, a displacement sensor 332, and an actuator 334 positioned within a housing 70" of each sensor component 20", 40". Each force sensor 330 may be operatively coupled to the displacement cylinder 76" of its respective sensor component 20", 40" and may generate an output signal, such as a voltage signal, indicative of a magnitude of force applied to its respective femoral paddle 32", 52". In one particular embodiment, each force sensor 330 may comprise a load cell such as miniature load cell.

Each displacement sensor 332 of its respective sensor component 20", 40" may generate an output signal indicative of respective displacement 230, 232 (FIG. 8) between its respective paddle set 24", 44". In some embodiments, each displacement sensor 332 may comprise an electrical device to generate electrical output signals indicative of the respective displacements 230, 232.

Each actuator 334 may be operatively coupled to a respective displacement cylinder 76" and may extend or retract the respective displacement cylinder 76" in response to a corresponding control signal. In one particular embodiment, each actuator 334 may comprise a stepper motor. In another embodiment, each actuator 334 may comprise a linear actuator. However, each actuator 334 may also be embodied as any prime mover devices operable to extend or retract the respective displacement cylinders 76".

Figure 7:
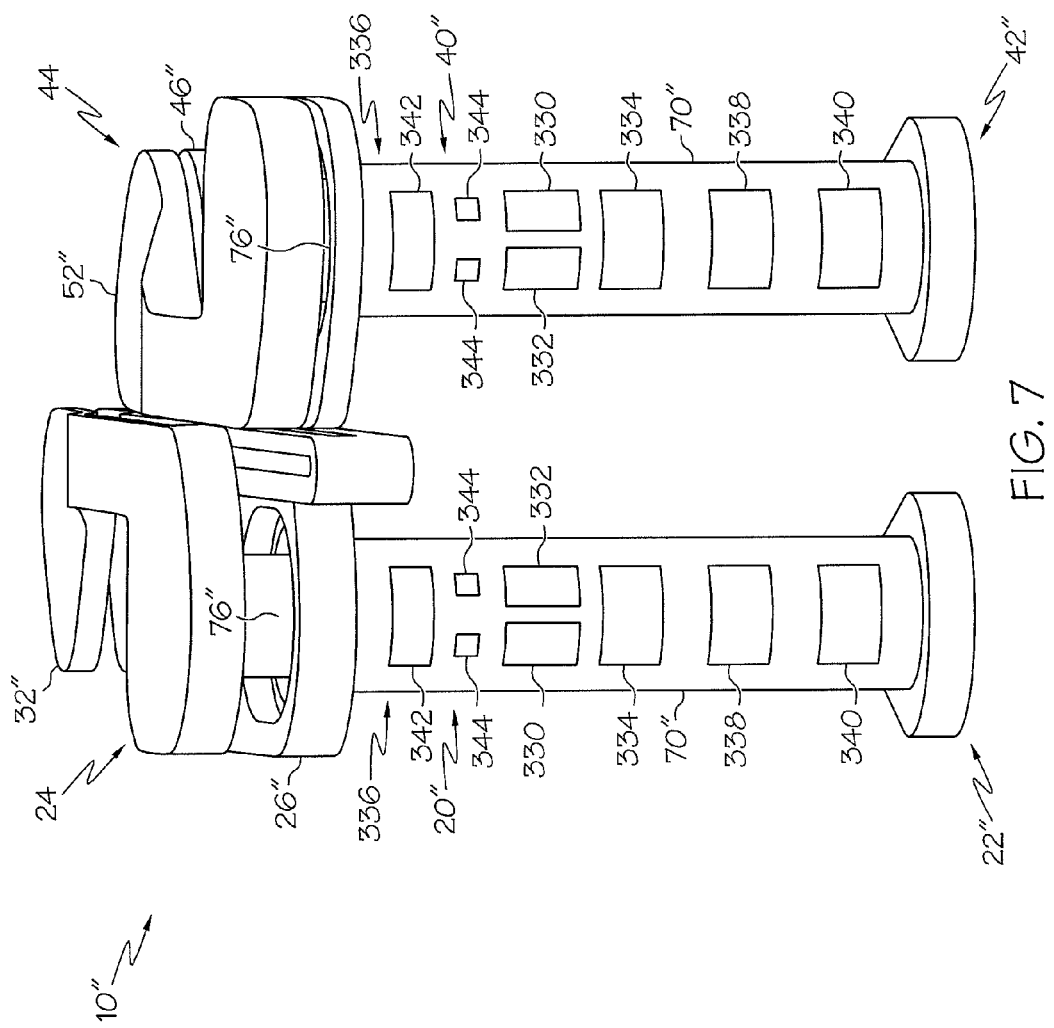
FIG. 7 shows a perspective view of yet another embodiment of a ligament balancer.

Each support 22", 42" of the ligament balancer 10" illustrated in FIG. 7 may also include a user interface 336, a controller 338, and a power supply 340 positioned on or in the respective housing 70". The user interface 336 may include a display screen 342 and a number of user buttons 344. In other embodiments, however, the display screens 342 may be replaced with a series of light-emitting-diodes (LEDs) or a collection of visual indicators to provide simplified visual feedback to the user of the ligament balancer 10". Additionally, in some embodiments, the user interfaces 336 may be replaced by a remote user interface(s) such as a user interface module that is separate from the supports 22", 42". In such an embodiment, the remote user interface(s) may communicate with the controllers 338 via wired or wireless communication.

Each controller 338 may comprise any type of controller including, for example, general purpose micro-controllers, microprocessors, or application specific integrated circuits (ASICs). Each power supply 340 may comprise any device capable of supplying power to the other respective components such as controllers 338. In one particular embodiment, the power supplies 340 may comprise replaceable batteries. In another embodiment, the power supplies 340 may comprise rechargeable battery packs. In such embodiments, the ligament balancer 10" may include appropriate charging contacts to allow the recharging of the battery packs. Although in the embodiment illustrated in FIG. 7, the ligament balancer 10" includes two user interfaces, two controllers, and two power supplies, it should be appreciated that in other embodiments the ligament balancer 10" may include only one user interface, one controller, and/or one power supply. For example, the ligament balancer 10" may include a single controller positioned in one of the supports 22", 42" and communicatively coupled to each of the force sensors 330, the displacement sensors 332, and the actuators 334. Similarly, the ligament balancer 10" may include a single user interface that is communicatively coupled to each of the controllers 338 (or to a single controller).

In use, the ligament balancers 10, 10', 10" may be inserted into a patient's knee via an medial, lateral or anterior approach. Referring now to FIG. 8, the ligament balancer 10 is shown with the sensor component 20 positioned such that the paddle set 24 extends beyond the paddle set 44 in the direction of extension D. In particular, the surgeon may slide the sensor component 20 with respect to the sensor component 40 such that the paddle set 24 extends beyond the paddle set 44 in the direction of extension D, thus configuring the sensor component 20 for a far side of the knee 200 that is away from the approach and the sensor component 20 for a near side of the knee 200 which is proximate the approach. It should be appreciated that FIG. 1 shows a converse configuration wherein the paddle set 44 extend beyond the paddle set 24 in the direction of extension D. Also, the sensor component 40 is not shown in FIG. 8 in order to not obscure the interaction between the sensor component 20 and the knee 200.

As shown in FIG. 8, extending the paddle set 24 beyond the paddle set 44 positions the posterior end 28 of the tibial paddle 26 to contact a portion 212 of the proximal tibia 210 which is away from the approach of the ligament balancer 10 into the knee 200. Moreover, the posterior end 34 is positioned to contact a condyle 222 of the distal femur 220 which is away from the approach. While not shown, extending the paddle set 24 beyond the paddle set 44 positions the posterior end 48 of the tibial paddle 46 to contact a portion 214 of the proximal tibia 210 which is near the approach or entry of the ligament balancer 10 into the knee 200. Moreover, the posterior end 54 is positioned to contact a condyle 224 of the distal femur 220 which is near the approach.

If the knee 200 were the right knee of a patient, then the depicted approach would be a medial approach. In which case, the portion 212 of the proximal tibia 210 corresponds to a lateral portion of the proximal tibia, the portion 214 of the proximal tibia 210 corresponds to a medial portion of the proximal tibia 210, the condyle 222 corresponds to a lateral condyle of the distal femur 220, and the condyle 224 corresponds to a medial condyle of the distal femur 220. In such a configuration, the sensor component 20 may be referred to as a lateral sensor component having a lateral paddle set to measure a lateral displacement and force between lateral portions of the proximal tibia 210 and distal femur 220. Likewise, the sensor component 40 may be referred to as a medial sensor component having a medial paddle set to measure a medial displacement and force between medial portions of the proximal tibia 210 and the distal femur 220.

It should be appreciated that sliding the sensor component 20 with respect to the sensor component 40 such that the paddle set 24 extends beyond the paddle set 44 in the direction of extension D as mentioned above, would also configure the ligament balancer 10 for a lateral approach of a patient's left knee. In which case, the portion 212 of the proximal tibia 210 corresponds to a medial portion of the proximal tibia 210, the portion 214 of the proximal tibia 210 corresponds to a lateral portion of the proximal tibia 210, the condyle 222 corresponds to a medial condyle of the distal femur 220, and the condyle 224 corresponds to a lateral condyle of the distal femur 220. In such a configuration, the sensor component 20 may be referred to as a medial sensor component having a medial paddle set to measure a medial displacement and force between medial portions of the proximal tibia 210 and distal femur 220. Likewise, the sensor component 40 may be referred to as a lateral sensor component having a lateral paddle set to measure a lateral displacement and force between lateral portions of the proximal tibia 210 and the distal femur 220.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

What is claimed is:

1. A method for balancing a knee, comprising:
   extending posterior ends of a first paddle set beyond posterior ends of a second paddle set along a general direction of extension, the first paddle set and the second paddle set being connected and slidable along the general direction of extension,
   inserting the posterior ends of the first paddle set and the second paddle set into a side of the knee without everting a patella of the knee,
   contacting, with the posterior ends of the first paddle set, portions of a proximal tibia and a distal femur that lie away from the side of the knee into which the posterior ends of the first paddle set were inserted, and
   contacting, with the posterior ends of the second paddle set, portions of the proximal tibia and the distal femur that lie toward the side of the knee into which the posterior ends of the second paddle set were inserted.

2. The method of claim 1, wherein extending posterior ends of a first paddle set includes sliding the first paddle set with respect to the second paddle set in the general direction of extension.

3. The method of claim 1, wherein inserting the posterior ends of the first paddle set and the second paddle set into a side of the knee includes inserting the posterior ends of the first paddle set and the second paddle set into a medial side of the knee.

4. The method of claim 3, wherein:
   contacting, with the posterior ends of the first paddle set, portions of a proximal tibia and a distal femur that lie away from the side of the knee into which the posterior ends of the first paddle set were inserted includes contacting a portion of the proximal tibia and a portion of the distal femur that lie toward a lateral side of the knee, and contacting, with the posterior ends of the second paddle set, portions of the proximal tibia and the distal femur that lie toward the side of the knee into which the posterior ends of the second paddle set were inserted includes contacting a portion of the proximal tibia and a portion of the distal femur that lie toward the medial side of the knee.

5. The method of claim 1, wherein inserting the posterior ends of the first paddle set and the second paddle set into a side of the knee includes inserting the posterior ends of the first paddle set and the second paddle set into a lateral side of the knee.

6. The method of claim 5, wherein:
contacting, with the posterior ends of the first paddle set, portions of a proximal tibia and a distal femur that lie away from the side of the knee into which the posterior ends of the first paddle set were inserted includes contacting a portion of the proximal tibia and a portion of the distal femur that lie toward a medial side of the knee, and
contacting, with the posterior ends of the second paddle set, portions of the proximal tibia and the distal femur that lie toward the side of the knee into which the posterior ends of the second paddle set were inserted includes contacting a portion of the proximal tibia and a portion of the distal femur that lie toward the lateral side of the knee.

7. The method of claim 1, further comprising:
measuring a first displacement between portions of the proximal tibia and the distal femur using the first paddle set, and
measuring a second displacement between portions of the proximal tibia and the distal femur using the second paddle set.

8. The method of claim 1, further comprising:
selecting a first force,
applying the first force between portions of the proximal tibia and the distal femur using the first paddle set,
selecting a second force, and
applying the second force between portions of the proximal tibia and the distal femur using the second paddle set.

9. The method of claim 8, wherein:
the first force is dependent upon a displacement between an upper end of a first displacement cylinder and a lower end of a first tensor cylinder, and
the second force is dependent upon a displacement between an upper end of a second displacement cylinder and a lower end of a second tensor cylinder.

10. The method of claim 9, wherein:
selecting the first force includes moving the first tensor cylinder in relation to the first displacement cylinder, and
selecting the second force includes moving the second tensor cylinder in relation to the second displacement cylinder.

11. The method of claim 10, wherein:
moving the first tensor cylinder includes unlocking the first tensor cylinder, and
moving the second tensor cylinder includes unlocking the second tensor cylinder.

12. The method of claim 8, further comprising:
outputting an indication of the first force to a user interface, and
outputting an indication of the second force to a user interface.

13. The method of claim 12, wherein:
the indication of the first force includes a first range of forces in which the first force lies, and
the indication of the second force includes a second range of forces in which the second force lies.

14. The method of claim 13, wherein:
the first range of forces is selected from a plurality of force ranges, and
the second range of forces is selected from the plurality of force ranges.

15. The method of claim 8, further comprising:
measuring a first displacement between portions of the proximal tibia and the distal femur using the first paddle set while applying the first force between portions of the proximal tibia and the distal femur, and
measuring a second displacement between portions of the proximal tibia and the distal femur using the second paddle set while applying the second force between portions of the proximal tibia and the distal femur.

16. A method for balancing a knee, comprising:
extending posterior ends of a first paddle set beyond posterior ends of a second paddle set along a general direction of extension, the first paddle set and the second paddle set being connected and slidable along the general direction of extension,
inserting the posterior ends of the first paddle set and the second paddle set into a medial side of the knee without everting a patella of the knee,
contacting, with the posterior ends of the first paddle set, portions of a proximal tibia and a distal femur that lie away from the medial side of the knee, and
contacting, with the posterior ends of the second paddle set, portions of the proximal tibia and the distal femur that lie toward the medial side of the knee.

17. The method of claim 16, further comprising:
selecting a first force,
applying the first force between portions of the proximal tibia and the distal femur using the first paddle set,
measuring a first displacement between portions of the proximal tibia and the distal femur using the first paddle set while applying the first force,
selecting a second force,
applying the second force between portions of the proximal tibia and the distal femur using the second paddle set, and
measuring a second displacement between portions of the proximal tibia and the distal femur using the second paddle set while applying the second force.

18. A method for balancing a knee, comprising:
extending posterior ends of a first paddle set beyond posterior ends of a second paddle set along a general direction of extension, the first paddle set and the second paddle set being connected and slidable along the general direction of extension,
inserting the posterior ends of the first paddle set and the second paddle set into a lateral side of the knee without everting a patella of the knee,
contacting, with the posterior ends of the first paddle set, portions of a proximal tibia and a distal femur that lie away from the lateral side of the knee, and
contacting, with the posterior ends of the second paddle set, portions of the proximal tibia and the distal femur that lie toward the lateral side of the knee.

19. The method of claim 18, further comprising:
selecting a first force,
applying the first force between portions of the proximal tibia and the distal femur using the first paddle set, measuring a first displacement between portions of the proximal tibia and the distal femur using the first paddle set while applying the first force, selecting a second force, applying the second force between portions of the proximal tibia and the distal femur using the second paddle set, and measuring a second displacement between portions of the proximal tibia and the distal femur using the second paddle set while applying the second force.

* * * * *